United States Patent [19]

Murphy

[11] 4,264,737

[45] Apr. 28, 1981

[54] METHOD OF MAKING GENETICALLY STABLE MUTANTS OF VIBRIO CHOLERAE

[75] Inventor: John R. Murphy, Cambridge, Mass.

[73] Assignee: President and Fellows of Harvard College, Cambridge, Mass.

[21] Appl. No.: 59,293

[22] Filed: Jul. 20, 1979

Related U.S. Application Data

[63] Continuation-in-part of Ser. No. 944,344, Sep. 21, 1978, abandoned.

[51] Int. Cl.³ .................. C12N 15/00; C12N 1/36; C12R 1/63
[52] U.S. Cl. .................. 435/172; 435/245; 435/909; 424/92
[58] Field of Search ........... 435/172, 245, 253, 909; 424/92, 93

[56] References Cited

U.S. PATENT DOCUMENTS

| | | | |
|---|---|---|---|
| 3,105,014 | 9/1963 | Harrison | 435/172 |
| 3,328,253 | 6/1967 | Watanabe | 424/92 |
| 3,984,285 | 10/1976 | Leuner | 435/172 |

OTHER PUBLICATIONS

Fetsailova et al., "N–Nitrosomethylurea Induced Streptomycin Dependent, and Strepto–, Mono–, and Neomycin resistant, Vibrio cholerae mutants and their properties", Chem. Absts., vol. 87, No. 9, p. 130 (1977), Abs. No. 63410a.

Mikhailova et al., "Studies on Vibrio Changes in the Presence of Antibiotics," Chem. Absts., vol. 88, No. 19 (1978), Abs. No. 131408d.

Mukerjee, "Preliminary Studies on the Development of a Live Oral Vaccine for Anti–Cholera Immunization", Bull. Org. mond. Sante, vol. 29, (1963), pp. 753–766.

Sanyal et al., "Live Oral Cholera Vaccine: Report of a Trial on Human Volunteer Subjects," Bull. Org. mond. Sante, vol. 40, (1969), pp. 503–511.

Finkelstein et al., "Studies on Toxinogensis in Vibrio cholerae, I. Isolation of Mutants with Altered Toxinogenicity", J. Infect. Dis., vol. 129, No. 2 (1974), pp. 117–123.

Vasil et al., "Conjugal Transfer of a Chromosomal Gene Determining Production of Enterotoxin in Vibrio cholerae," Science, vol. 187, (1975), pp. 849–850.

Mekalanos et al., "Affinity Filters, a New Approach to the Isolation of Tox Mutants of Vibrio cholerae," Proc. Nat'l. Acad. Sci., vol. 75, No. 2 (1978), pp. 941–945.

Holmes et al., "Quantitative Measurements of Cholera Enterotoxin in Cultures of Toxogenic Wild–Type and Nontoxinogenic Mutant Strains of Vibrio cholerae by Using a Sensitive and Specific Reversed Passive Hemagglutination Assay for Cholera Enterotoxin," Infection and Immunity, vol. 19, No. 1, (1978), pp. 101–106.

Ruch et al., "Isolation of Nontoxinogenic Mutants of Vibrio cholerae in a Colorometric Assay for Cholera Toxin using the S49, Mouse Lymphosarcoma Cell Line," J. Infect. Dis., vol. 137, No. 6 (1978) pp. 747–755.

Primary Examiner—Thomas G. Wiseman

[57] ABSTRACT

Incubation of a parent strain of Vibrio cholerae at elevated temperature to produce a hypotoxinogenic variant strain and mutation of the variant strain results in mutant strains which retain the biotype and antigens of the parent strain, and which are genetically stable and useful as live oral vaccines for immunization against cholera. Preferably, a hypotoxinogenic mutant which is also non-pathogenic in animal model systems is isolated by the method disclosed in this application.

6 Claims, No Drawings

METHOD OF MAKING GENETICALLY STABLE MUTANTS OF VIBRIO CHOLERAE

This application is a continuation-in-part of applicant's U.S. patent application Ser. No. 944,344, abandoned, filed Sept. 21, 1978.

This invention described herein was made in the course of work under a grant or award from the Department of Health, Education and Welfare.

This invention relates to a method of making genetically stable mutants of *Vibrio cholerae* which produce a defective cholera toxin and are suitable for the production of a live oral vaccine for immunization against cholera.

It is widely known that the profuse watery diarrhea of cholera results from the action of cholera toxin on the epithelial cell lining of the small intestine. Cholera toxin is elaborated from toxinogenic strains of *V. cholerae*. Toxinogenic strains may be either the classical or el tor biotype and the Oqawa or Inaba serotype; however, in all instances so far examined the toxin produced by these different types appears to be the same.

Over the past decade a number of different cholera vaccines have been developed and tested by field trial. In general, these vaccines have been composed of either killed whole cell preparations, cell wall preparations, or most recently a toxoid prepared from the formalin or glutaraldehyde inactivation of purified toxin. The prior vaccines were administered parenterally and the results from field trials have been disappointing in that the protection against disease has been short lived for only a fraction of the population immunized. It is clear, however, that cholera patients are well protected against re-infection, or challenge with toxinogenic *V. cholerae* for up to one year.

The first attempts toward the development of a live oral vaccine against cholera, analogous to the Sabin polio vaccine, with the desirable property of self-replicating antigens, were made by Mukerjee and co-workers (Mukerjee, Bull. Org. Mond. Sante (Bull. Wld. Hlth. Org.), Vol. 29, 753–766, 1963; Sanyal and Mukerjee, Ibid., Vol. 40, 503–511, 1969) who used non-toxinogenic El Tor vibrios isolated from nature. These strains were found to be effective in inducing circulating vibriocidal as well as general intestinal antibodies. Protection against disease, however, was poor owing to an apparent failure of these organisms to colonize the small bowel. The isolation of genetically stable non-toxinogenic mutants of *V. cholerae* has been the approach of Finkelstein and coworkers (Finkelstein et al. The J. of Infectious Diseases, Vol 129, 117–123, 1974; Vasil et al., Science, Vol 187, 849–850, 1975). Mutants of toxinogenic *V. cholerae* which gave no evidence of producing antigenically reaction toxin were selected by immunological methods. One such mutant has recently been evaluated in human volunteers. Oral administration of 3-4 doses ($10^{10}$ bacteria/dose) of "non-virulent" organisms was followed by oral challenge with $10^6$ virulent cholera bacilli six weeks after immunization. The volunteers that received the oral immunization showed a 55% rate of protection as compared to the control group. Among the 66 volunteers receiving the vaccine, 84% showed a rise in serum vibriocidal antibody titres and, curiously 26% showed an increase in serum antitoxin titres. It is now known that this mutant strain M-13, produces low levels of biologically active holocholera toxin. Furthermore, highly toxinogenic strains of *V. cholerae* were isolated from the stools of some of the volunteers who were immunized. This strongly suggests that this mutant strain was genetically unstable.

Many mutant strains of *V. cholerae* 569B that produce low levels of biologically active toxin have been isolated, but most all the mutants that have been isolated by single step methods have produced either low or elevated levels of holocholera toxin, as pointed out by Mekalanos et al., Proc. Natl. Acad. Sci. USA, Vol. 75, 941–945, 1978 and by Holmes et al., Infection and Immunity, Vol. 19, 101–106, 1978. As a class these mutant strains have been regarded as cholera tox regulatory mutants, rather than mutants with an alteration in the structural gene for either Subunit A or Subunit B of toxin. Most all of the mutants that have been described have also been found to have reverted to "wild-type" toxinogenicity at a measurable frequency either in vitro and/or in vivo.

It has now been found that genetic stability of mutant strains of *V. cholerae* can be ensured by a two step process, one of which is induced by incubating a strain at elevated temperature to produce a variant having both hypotoxinogenicity and genetic stability, and the second is mutagenesis and selection of strains with decreased toxicity. Preferably, the selected mutants would also be non-pathogenic.

The heat-induced variant is preferably first formed by incubating a standard parent strain of *V. cholerae*, such as the widely available *V. cholerae* 569B, to produce a strain which is hypotoxinogenic as assayed in S49 mouse lymphosarcoma cells, the toxicity being reduced by a factor of more than 750, preferably by a factor of about 1000, and which is genetically stable. The incubation temperature is from 40° to 42° C.; at 43° C., there is no growth of the cells. The time of incubation is not critical, a matter of several hours usually being required for adequate growth, preferably from 15 to 20 hours. A hypotoxinogenic strain thus induced is then subjected to a second mutation by any conventional mutagenesis, either by a chemical mutagen or by irradiation, preferably the former. Mutant strains thus produced are found to retain the biotype and antigens of both the original *V. cholerae* strain (e.g., 569B) and the heat-induced variant, but differ from them in that their toxicity is further reduced. These mutant strains display a further reduction in toxicity, being decreased by a factor of at least 7500, usually from 7500–15000, with respect to the original or parent strain, and also display genetic stability both in vitro and in vivo, being capable of colonizing the gastrointestinal system. Further selection of non-pathogenic mutants may be made following challenge of rodent and porcine animal model systems used for the determination of choleragenicity. These non-pathogenic mutants would be consequently useful as live oral vaccines for immunization against cholera.

The heat-induced variant strains can readily be assayed for reduced toxicity by the same S49 mouse lymphosarcoma cell assay commonly used for *V. cholerae* mutants. The conventional rabbit skin permeability factor assay as well as the Y-1 adrenal cell assay may also be used to assay toxicity of both the variants and the mutants, thus providing alternative means for selecting the variant and mutant colonies having the desired hypotoxinogenic properties.

The following examples are intended to illustrate more fully the nature of the invention without acting as a limitation upon its scope.

EXAMPLES

Cultures of the widely available *V. cholerae* strain 569B were grown in Syncase medium in Erlenmeyer flasks (culture volume 10% flask volume) at 30° C. for 18-20 hours with vigorous aeration. Large volumes (5-10 l) were grown in a Microferm Fermentor (New Brunswick Scientific Co., Inc., Edison, N.J.) at 30° C., sparged with air at 0.5 l/min/l of culture, and agitated at 700 r.p.m. for 18-20 hours. Bacteria were sedimented at 10,000×g for 20 minutes and crude culture supernatant fluids were filtered through a 0.45μ membrane (Millipore Corp., Bedford, Mass). Culture filtrates were concentrated 40-100-fold by pressure ultrafiltration on PM-10 membranes (Amicon Corp., Lexington, Mass).

Isolation of heat induced hypotoxinogenic variants

*V. cholerae* 569B was grown in Syncase broth for 18 hours at 42° C. Nutrient agar plates were inoculated by spreading dilutions of the culture and incubated overnight at 30° C. Single colonies were used to inoculate separate wells of a microtitre plate (Linbro, 76-003-05, Hamden, Conn.) containing 250 μl Syncase broth. Microtitre plates were incubated at 30° 1 C. for 24 hours, the bacteria were sedimented by centrifugation, and 10 μl volumes of culture supernatant fluid were assayed for cholera toxin activity by the S49 lymphosarcoma cell assay. This procedure resulted in the isolation of hypotoxinogenic variants at a frequency of 0.3%. Three of these variants were found to have approximately 0.010-0.020 μg of cholera toxin equivalents per ml of culture filtrate when grown under optimal conditions for toxin production and assayed in 2-fold serial dilutions of concentrated culture supernatant fluids, as compared to a CT activity of 15 μg/ml for the parent strain *V. cholerae* 569B. The in vitro genetic stability of the heat-induced variant strains was determined by monitoring toxicity in the S49 lymphosarcoma cell assay after serial daily passage in Syncase broth (1/50 dilution of a 24 hour culture into fresh medium). No increase in the level of toxin production was observed over a two week period of serial passage.

The isolated variant was grown in Syncase broth and logarithmic phase cells were mutagenized with N-methyl-N'-nitro-nitrosoguanidine (60 μg/ml) for 10-30 minutes. Surviving bacteria were sedimented by centrifugation, washed, resuspended in fresh medium, and incubated at 30° C. for 1 hour. Nutrient agar plates were inoculated, incubated at 30° C., and single colonies were transferred to separate wells of microtitre plates. Following overnight incubation culture supernatant fluids were assayed for cholera toxin activity as described above. Potential mutant strains were streaked on Nutrient agar plates and 12 single colonies of the 600 examined were retested for toxicity in the S49 lymphosarcoma cell assay. Twenty-five fold concentrated culture supernatant fluids of these potential mutant strains were found to be nontoxic in both the S49 lymphosarcoma cell and Y-1 adrenal cell assays for cholera toxin; however, 50-100-fold culture concentrates were toxic in the Y-1, S49, and rabbit skin permeability factor assays. All of the nitrosoguanidine induced mutant strains were found to produce between 1 and 15 ng cholera toxin equivalents/ml culture supernatant fluid. Mutant strains were serially designated *V. cholerae* 569B(tox TI-101N1) to 569B(tox TI-101N12) according to the order of isolation.

Detection and quantitation of cholera toxin, Subunit B, and Subunit A

Cholera toxin. Cholera toxin was assayed qualitatively and quantitatively by the S49 mouse lymphosarcoma cell assay and in the Y-1 adrenal cell assay essentially as previously described. In addition, quantitative measurements of cholera toxin were made by the rabbit skin permeability factor assay.

Subunit B. Subunit B of cholera toxin was assayed by counter immunoelectrophoresis of 2-fold serial dilutions of concentrated culture supernatant fluids against purified anti-Subunit B. Anti-Subunit B was purified from anticholeragenoid by affinity chromatography on a Subunit B-Sepharose 4B column.

Subunit A. The enzymic activity of Subunit A of cholera toxin was also measured essentially by previously known procedures. Freshly drawn pigeon erythrocytes were washed and passed through a column of absorbant cotton to remove contaminating leukocytes. Pelleted erythrocytes (1200×g, 5 minutes) were resuspended in an equal volume of medium A (130 mM NaCl, 5 mM KCl, 2 mM MgCl$_2$, 20 mM Hepes, pH 7.3) and lysed by rapid freeze thaw. 50 μl aliquots of the erythrocyte lysate were incubated with sodium dodecyl sulfate (SDS) activated samples for 30 minutes at 37° C. Activated erythrocyte ghosts were then sedimented at 1200×g for 10 minutes and incubated for an additional 30 minutes at 37° C. in a cyclic adenosine monophosphate (cAMP) accumulation medium which contained 0.2 mM theophylline, and cAMP levels were measured by previously known procedures. Subunit A of cholera toxin was also measured by reversed passive hemagglutination using anti-SA as previously described.

Cholera toxin, Subunit B, and Subunit A activity were assayed as described above for *V. cholerae* 569B, the selected heat-induced variants and a number of selected mutants. The mutant strains that have been characterized may be classified into three groups based upon the nature of their cholera tox gene products. The first group is represented by *V. cholerae* 569B (tox TI-101N4) which was found to produce the same level of Subunit A activity per ml of culture supernatant fluid as the parent heat-induced variant strain, but does not produce detectable levels of Subunit B in 100-fold culture concentrates (Table 2). *V. cholerae* 569B(tox TI-101N9) is representative of the second group. This strain was found to produce 10-fold lower levels of Subunit A activity per ml of culture filtrate than the parent strain. The third group is represented by *V. cholerae* 569B (tox TI-101N3) and 569B(tox TI-101N5). These two strains have been found to produce slightly lower levels of Subunit A activity per ml than the heat induced variant parent strain. The results are summarized in the following table:

CHOLERA TOXIN, SUBUNIT A, AND SUBUNIT B ACTIVITY IN CULTURE SUPERNATANT FLUIDS OF *VIBRIO CHOLERAE* 569B, A HEAT INDUCED VARIANT, AND MUTANT STRAINS.

| V. cholerae strain | μg/ml CT activity | | Subunit B μg/ml CT equivalents | Subunit A μg/ml CT equivalents |
|---|---|---|---|---|
| | S49 mouse lymphosarcoma cell assay | rabbit skin permeability factor assay | | |
| 569B | 15 | 15 | 15 | 15 |
| Heat-induced variant | 0.010–0.015 | 0.015–0.025 | 0.001 | 3 |
| 569B(tox TI-101N3) | 0.006–0.010 | 0.015–0.020 | <0.02 | 1 |
| 569B(tox TI-101N4) | 0.001–0.005 | 0.004 | <0.0005 | 3 |
| 569B(tox TI-101N5) | 0.002–0.010 | 0.006 | <0.02 | 1 |
| 569B(tox TI-101N9) | 0.001–0.005 | 0.015–0.029 | <0.02 | 0.3 |

The mutant *V. cholerae* 569B(tox TI-101N4) is characterized as follows:
  Gram negative motile rod
  Classical biotype
  Inaba serotype +
  Group serotype +
  Generation time approximately 48 minutes in Syncase broth
  Biochemical reactions:
    β-galactosidase— —
    arginine dihydrolyase— —
    lysine decarboxylase— +
    orinithine decarboxylase— +
    citrate utilization— —
    hydrogen sulfide production— —
    urease— —
    tryptophane deaminease— —
    indole production— +
    acetoin production— —
    gelatin liquefaction— +
    mannitol utilization— +
    inositol utilization— —
    sorbitol utilization— —
    rhamnose utilization— —
    sucrose utilization— +
    melibiose utilization— —
    amygdalin utilization— —
    (1+) arabinose utilization— —
    glucose utilization— +
    catalase production— —
  Grows on TCBS agar.

The genetic stability of the mutant *V. cholerae* 569B(tox TI-101N4) has been tested in vivo by colonizing the mutant strain in germ free rats. *V. cholerae* was isolated from the feces on alternate days. Two hundred randomly selected colonies were tested for toxinogenicity from each sampling. After 5 weeks of testing no revertants were detected, strongly indicating that revertants do not have a selective advantage in the colonization of the rat gastrointestinal system; and furthermore, if reversion to "wild-type" did occur, the rate was below the level of screening. The mutant retains the biotype and antigens of the parent strain and is capable of colonizing the small intestine of rabbits.

Further analysis of *V. cholerae* tox TI-101N4 was made by oral challenge of hysterectomy produced colostrum--deprived 2 week old piglets. The parental strain, *V. cholerae* 569B was used as the positive control.

Within 6 hours following the administration of $4 \times 10^6$ viable *V. cholerae* 569B the stool became soft. Diarrhea began within 15 hours and the profuse watery diarrhea characteristic of severe cholera began within 24 hours. Clinical disease lasted for up to 5 days.

In contrast, oral challenge of the piglets with $4 \times 10^9$ viable *V. cholerae* tox TI-101N4 did not produce any symptoms of enteric disease. Viable organisms could be isolated from the stool of healthy piglets up to day seven when the animals were sacrificed. Upon autopsy piglets challenged with *V. cholerae* tox TI-101N4 were found to be normal.

The isolation of genetically stable mutants of heat-induced variants offers the advantage of a two-step genetic alteration. If the frequency of reversion is on the order of $10^{-8}$ for the heat induction step and $10^{-8}$ for the mutational step, then the rate of reversion of mutants to "wild-type" should be $10^{-16}$. This offers a high degree of confidence in the safety of such a live oral vaccine strain. The importance of genetic stability for such a strain cannot be overemphasized for scientific, ethical, and political reasons.

What is claimed is:

1. The process of producing a hypotoxinogenic and genetically stable variant strain of *Vibrio cholerae* which comprises incubating a parent strain of *V. cholerae* at at a temperature of 40° to 42° C. and selecting therefrom a variant strain retaining the biotype and antigens of the parent strain and having a toxicity, as assayed in S49 mouse lymphosarcoma cells, reduced by a factor of at least 750.

2. The process as claimed in claim 1 in which the strain is *V. cholerae* 569B.

3. The process as claimed in claim 1 comprising the additional steps of subjecting said variant strain to mutagenesis by exposure to a chemical mutagen or to irradiation and selecting a mutant strain having a toxicity, as assayed in S49 mouse lymphosarcoma cells, reduced from that of said parent strain by a factor of at least 7500.

4. The process as claimed in claim 3 in which said mutagenesis is chemical.

5. The process as claimed in claim 2 comprising the additional steps of subjecting said variant strain to mutagenesis by exposure to a chemical mutagen or to irradiation and selecting a mutant strain having a toxicity, as assayed in S49 mouse lymphosarcoma cells, reduced from that of said parent strain by a factor of at least 7500.

6. The process as claimed in claim 5 in which said mutagenesis is chemical.

* * * * *

UNITED STATES PATENT AND TRADEMARK OFFICE
CERTIFICATE OF CORRECTION

PATENT NO. : 4,264,737
DATED : April 28, 1981
INVENTOR(S) : John R. Murphy

It is certified that error appears in the above-identified patent and that said Letters Patent are hereby corrected as shown below:

Column 1, line 55, "reaction" should be --reactive--;

Col. 3, line 26, after "30°", delete "1".

Signed and Sealed this

Eleventh Day of August 1981

[SEAL]

Attest:

Attesting Officer

GERALD J. MOSSINGHOFF

Commissioner of Patents and Trademarks